United States Patent
Tanaka et al.

(10) Patent No.: US 9,441,193 B2
(45) Date of Patent: *Sep. 13, 2016

(54) CELL CULTURE APPARATUS, CELL CULTURE SYSTEM AND CELL CULTURE METHOD

(75) Inventors: Satoshi Tanaka, Kanagawa (JP); Yoichi Ishizaki, Kanagawa (JP); Ryo Suenaga, Kanagawa (JP); Yoriko Tokita, Kanagawa (JP); Masahito Kogure, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 836 days.

This patent is subject to a terminal disclaimer.

(21) Appl. No.: 12/450,481

(22) PCT Filed: Apr. 25, 2008

(86) PCT No.: PCT/JP2008/058008
§ 371 (c)(1),
(2), (4) Date: Sep. 28, 2009

(87) PCT Pub. No.: WO2008/136371
PCT Pub. Date: Nov. 13, 2008

(65) Prior Publication Data
US 2010/0075406 A1    Mar. 25, 2010

(30) Foreign Application Priority Data
Apr. 27, 2007   (JP) ................................. 2007-119112

(51) Int. Cl.
*C12M 1/34* (2006.01)
*C12M 1/00* (2006.01)
(Continued)

(52) U.S. Cl.
CPC ............ *C12M 23/34* (2013.01); *C12M 23/14* (2013.01); *C12M 27/02* (2013.01); *C12M 29/00* (2013.01); *C12M 33/18* (2013.01)

(58) Field of Classification Search
CPC .... C12M 41/26; C12M 41/32; C12M 41/44; C12M 23/14; C12M 23/26; C12M 27/02; C12M 29/26; C12M 23/34; C12M 33/18; C12M 29/00; C23M 23/14; C23M 23/26; C23M 27/02; C23M 29/26
USPC .......................................... 435/287.1, 289.1
See application file for complete search history.

(56) References Cited

U.S. PATENT DOCUMENTS 4,829,002 A * 5/1989 Pattillo et al. ............. 435/297.1
5,017,490 A    5/1991 Taiariol et al.
(Continued)

FOREIGN PATENT DOCUMENTS

JP    2000-125848 A    5/2000
JP    2002504363 A    2/2002
(Continued)

OTHER PUBLICATIONS

Machine Translation of JP 2000-125848, retrieved Mar. 24, 2012.*
(Continued)

*Primary Examiner* — William H Beisner
*Assistant Examiner* — Danielle Henkel
(74) *Attorney, Agent, or Firm* — Osha Liang LLP

(57) ABSTRACT

By maintaining the cell density during culture at an appropriate level and eliminating the procedure of transferring cells from a container to another container when a large amount of cells are cultured, damage on cells can be reduced, risk of contamination can be lowered, labor saving can be attained and automation can be attained.

A cell culture apparatus including: a culture container 11 formed of a soft packing material and having an enclosure part 11-1 in which a culture medium and/or cells being cultured are enclosed is placed; a container table 12 on which the culture container 11 is placed; a roller 13 which is placed on the upper surface of the culture container 11 and divides the enclosure part 11-1 into two or more chambers; and a driving means 15 which relatively moves the roller 13 or the culture container 11, thereby to change the volume of the culture part 11-11 in the enclosure part 11-1 in which a culture medium or cells being cultured are enclosed.

16 Claims, 14 Drawing Sheets

(51) Int. Cl.
  *C12M 1/06* (2006.01)
  *C12M 1/26* (2006.01)

(56) References Cited

U.S. PATENT DOCUMENTS

| | | | |
|---|---|---|---|
| 5,079,168 A * | 1/1992 | Amiot | 435/297.2 |
| 5,126,238 A | 6/1992 | Gebhard et al. | |
| 5,316,905 A | 5/1994 | Mori et al. | |
| 5,416,022 A | 5/1995 | Amiot | |
| 5,554,093 A * | 9/1996 | Porchia et al. | 493/240 |
| 6,369,394 B1 | 4/2002 | Lee | |
| 6,391,638 B1 | 5/2002 | Shaaltiel | |
| 6,461,853 B1 | 10/2002 | Zhu | |
| 2004/0254559 A1 | 12/2004 | Tanaami et al. | |
| 2005/0054101 A1 | 3/2005 | Felder et al. | |
| 2005/0084961 A1 | 4/2005 | Hedrick et al. | |
| 2007/0037276 A1 * | 2/2007 | De Crecy | 435/293.1 |
| 2007/0048859 A1 * | 3/2007 | Sears | 435/289.1 |
| 2010/0062530 A1 * | 3/2010 | Tanaka | C12M 41/26 435/383 |

FOREIGN PATENT DOCUMENTS

| | | | |
|---|---|---|---|
| JP | 2004-89136 A | 3/2004 | |
| WO | WO 98/13469 A1 | 4/1998 | |
| WO | WO9943790 * | 2/1999 | .............. C12N 7/04 |
| WO | WO 2005/083052 A1 | 9/2005 | |

OTHER PUBLICATIONS

Chinese Patent Office, "Office Action for CN 200880013451.1", Oct. 15, 2012.
Japan Patent Office, "Office Action for 2009-512957", Apr. 16, 2013.
European Patent Office, "Extended European Search Report for EP 08 75 2082", May 27, 2013.
Korean Office Action in corresponding Korean Application No. 10-2009-7021714 mailed Aug. 26, 2014 (8 pages).

* cited by examiner (a) Top view (b) Side view

FIG.10 (A single cassette product)

FIG.12

| Culture time (hr) | Area of culture part (cm)$^2$ | Amount of culture medium (ml) |
|---|---|---|
| 0 | 120.4 | 100 |
| 8 | 129.0 | 110 |
| 16 | 137.6 | 120 |
| 24 | 146.2 | 130 |
| 30 | 163.4 | 147 |
| 36 | 180.6 | 164 |
| 42 | 197.8 | 181 |
| 48 | 215.0 | 198 |
| 54 | 240.8 | 227 |
| 60 | 266.6 | 256 |
| 66 | 292.4 | 285 |
| 72 | 318.2 | 314 |
| 78 | 344.0 | 357 |
| 84 | 369.8 | 400 |
| 90 | 395.6 | 443 |
| 96 | 430.0 | 486 |
| 120 | 430.0 | 500 |

FIG. 13

| | Number of seeded cells | Number of cells after 120 hour culture | Proliferation ratio |
|---|---|---|---|
| Example 1 | $1.0 \times 10^7$ | $4.3 \times 10^8$ | 43 times |
| Comparative Example 1 | $1.0 \times 10^7$ | $3.3 \times 10^8$ | 33 times |

CELL CULTURE APPARATUS, CELL CULTURE SYSTEM AND CELL CULTURE METHOD

TECHNICAL FIELD

The present invention relates to a cell culture apparatus for culturing cells, tissues, microorganisms or the like under an artificial environment, a cell culture system provided with the cell culture apparatus and a cell culture method in the cell culture apparatus or the cell culture system. In particular, the present invention relates to a cell culture apparatus, a cell culture system and a cell culture method which are suitable for reducing damage on cells, lowering the risk of contamination, saving labor and automating the process by maintaining the cell density at an appropriate level during the culture and eliminating the procedure of transferring cells from one culture container to another when a large amount of cells are cultured.

BACKGROUND ART

Cell culture is a technology of taking tissues of skin, lung or kidney or cells such as lymphocytes and leukemia cells out of a living body and growing and keeping them alive in vitro.

With the development of cell culture technology in recent years, its application not only for the elucidation of life phenomena but also for the manufacture of virus vaccine, the production of biological medicines, the gene therapy or regenerative medical therapy and the immuno-cell therapy has been studied and implemented.

The conventional procedure of cell culture performed in the immuno-cell therapy is explained with reference to FIG. 14.

In the conventional cell culture method, cells were cultured while transferring (subculture) the cells to another cell culture container having a larger volume with the proliferation of the cell.

Specifically, as shown in the figure, at first, 30 cc of a culture medium (here, it contains $10^7$ immune cells) is put in a cell culture flask (hereinafter simply referred to as "flask").

In this culture, the temperature, carbon dioxide concentration ($CO_2$) and humidity are set at 37° C., 5% and 95%, respectively.

Three days after, the volume of the culture medium in the flask was increased in an amount of 30 cc to 60 cc, and four days after, the volume of the culture medium was further increased in an amount of 60 cc to 120 cc. In view of the relationship between the flask volume and the cell density, the culture medium is transferred to another cell culture container. Here, two flasks are newly provided, and subculture is conducted such that each flask is charged with 40 cc of the culture medium.

When the culture medium in each flask is increased from 40 cc in an amount of 40 cc to become 80 cc, then, the culture medium in each of the three flasks is transferred to one cell culture bag (hereinafter simply as a "bag"). 240 cc (80 cc×3) of the culture medium, cells being cultured and 1000 cc of a fresh culture medium are enclosed in this bag, and cultured for two days. Furthermore, in respect of the relationship between the volume of the bag and the cell density, a bag is newly provided and subculture is conducted such that each bag is charged with 620 cc of the culture medium.

Then, in each bag, 500 cc of a fresh culture medium is added to the 620 cc of the culture medium to make the total volume thereof 1120 cc, and culture is conducted. Thereafter, two bags are newly provided, and subculture is conducted such that each bag is charged with 560 cc of the culture medium.

As mentioned above, by sequentially transferring a culture medium to a culture container having a larger volume or by increasing the number of a container, an appropriate culture environment can be maintained.

The reason for transferring cells is as follows. When the cell density is low when culture is started, proliferation of cells is suppressed. Therefore, when cells are cultured on a certain scale, it is common to culture the cell while repeating subculture so that the cell density can be maintained appropriately.

However, this method makes the procedure complicated since part cells being cultured has to be transferred to a new flask or bag (or a dish) whenever subculture is conducted. In addition, this method has a higher degree of probability of being contaminated with various bacteria.

Under such circumstances, a method can be conceived in which cells are caused to proliferate in a bag, and when the cells are proliferated, a new bag filled with a fresh culture medium is connected to attain uniformity. By this method, the risk of being contaminated by various bacteria can be lowered.

However, it appears that this procedure takes a certain period of time until uniformity is attained. The larger the internal volume of the culture bag, the longer the time required for attaining uniformity. The procedure becomes complicated, although it is less complicated as compared with the procedure in the open system. In addition, the quantity of cell culture equipment to be consumed is increased.

Under such circumstances, various technologies are proposed to maintain an appropriate culture environment without conducting subculture. For example, a cell culture bag has been disclosed which is provided with prohibiting members by which the bag is partitioned so that the circulation of the culture medium in the bag is prohibited (see Patent Document 1, for example).

In this technology, the region in the bag where culture is actually conducted can be gradually extended. Therefore, culture can be conducted continuously within the same bag from the start to the end. In this technology, the fear of contamination with various bacteria can be eliminated, culture can be conducted taking into consideration the cell density at the time of starting culture or during culture depending on the proliferation capability of cells, and cells can be cultured efficiently by means of simple equipment.

Also disclosed is a cell culture system comprising an external partition member (a partitioning clamp) for dividing a single bag-like enclosure into sub-compartments (see Patent Document 2, for example).

According to this culture system, a plurality of sub-compartments can be provided by squeezing part of the bag-like enclosure by means of the external partition member. Therefore, it is possible to provide means to proliferate cells to a number enough to be introduced into the production system under conditions which provide a small-scale starting environment for ensuring the viability of cells and a necessary environment which is enlarging in scale.

Also disclosed is a culture container provided with an elastically deformable tubular culture container and a clip capable of squeezing the culture container at an arbitral position (see Patent Document 3, for example).

According to this culture container, it is possible to increase the internal volume of the culture container by shifting the position of the clip according to the growth of cells.

Patent Document 1: JP-A-2000-125848

Patent Document 2: Japanese Patent No. 2981684 (page 5)

Patent Document 3: JP-A-2004-89136 (page 5, paragraph [0021] and FIG. 3)

DISCLOSURE OF THE INVENTION

Problem to be Solved by the Invention

Cell proliferation is conducted continuously. However, in the conventional technologies as disclosed in Patent Documents 1 to 3, since the culture area is enlarged intermittently, it was difficult to change the volume continuously in accordance with the status of cell culture.

In addition, since each of the conventional technologies was manually conducted, the procedure thereof was complicated.

The technology disclosed in Patent Document 3 is used for the proliferation of mesenchymal stem cells. The proliferation speed of mesenchymal stem cells, which proliferate while being adhered to the bottom surface of a culture container, varies depending on the spatial culture environment under which it is placed. Specifically, since mesenchymal stem cells proliferate while being adhered to the bottom surface of the culture container, the bottom surface of the culture container has to be wide enough for the cells to adhere. However, if the bottom surface is too wide, the speed of proliferation is lowered, making efficient cell growth of difficult.

If each conventional technology is used, the position of the partition means in the culture bag is determined by the intuition or experiences of a user. Therefore, it was impossible to attain equally efficient growth of cells.

The present invention has been made in view of the above-mentioned circumstances, and an object thereof is to provide a cell culture apparatus, a cell culture system and a cell culture method which can reduce the damage on cells, lower the risk of contamination, save labor and automate the process by maintaining the cell density at an appropriate level during culture and by eliminating the procedure of transferring cells from one container to another when a large amount of cells are cultured.

Means for Solving the Problem

In order to attain the object, the cell culture apparatus of the present invention is a cell culture apparatus comprising:
a container table on which a culture container formed of a soft packing material and having an enclosure part in which a culture medium and/or cells being cultured are enclosed is placed;
a movable partition member which is placed on the upper surface of the culture container and divides the enclosure part into two or more chambers; and a driving means which moves the partition member and/or the culture container, thereby to change the volume of each of the chambers divided by the partition member.

Due to such a configuration of the cell culture apparatus, the volume of a part of the enclosure part in which a culture medium or cells being cultured are enclosed (culture part) can be continuously changed. This allows the cell density to be maintained at an appropriate level by moving the partition member or the culture container so as to increase the volume of the culture part even when the cell density is increased by the proliferation of cells during culture. In addition, when proliferated cells are harvested, the volume of the culture part is reduced by moving the partition member or the culture container, and, as a result, cells being cultured are pushed out of the enclosure part and harvested.

In the cell culture apparatus of the present invention, a roller is used as the partition member. By utilizing the rotational movement of a roller, the volume of the culture part can be changed not intermittently but continuously. Under the circumstances where cells are constantly proliferated, the roller or the container table are allowed to move according to the degree of cell proliferation so as to change the volume of the culture part, whereby the cell density can always be maintained at an appropriate level.

In addition, the partition member such as a roller can be moved with a culture medium or the like being enclosed in the culture container, which enables the cell culture to be performed in a closed system in which only one culture container is used. In the cell culture in the closed system, cells being cultured are prevented from being in contact with the outside, whereby damage on cells can be reduced and risk of contamination can be lowered.

In addition, since the volume of the culture part of the culture container can be changed by the movement of the partition member such as a roller, conventional subculture operations can be avoided, whereby a significant degree of labor saving can be attained.

Further, the cell culture apparatus of the present invention may have a configuration in which it is provided with a measuring means for measuring the condition of a culture medium and/or cells being cultured, wherein the driving means allows the partition member and/or the culture container to move based on measurement results obtained by the measuring means.

Due to such a configuration of the cell culture container, the partition member such as a roller can be moved based on the state of a culture medium or cells being cultured. As a result, the volume of the culture part of the culture container can be automatically changed, whereby the cell density during culture or the culture environment can be appropriately maintained.

The cell culture apparatus of the present invention is provided with a trough-like member having an arc-shaped cross section and is provided outside the outer peripheral surface of the roller, and the culture container is held between the roller and the trough-like member so as to divide the enclosure part into two or more chambers.

Due to such a configuration of the cell culture apparatus, by holding the both surfaces of the culture apparatus between the roller and the trough-like member, it is possible to allow the culture part of the enclosure part to have an appropriate volume. In addition, by moving the roller and the trough-like member in the same direction with the culture apparatus being held therebetween, the volume of the culture part can be changed, whereby the cell density of the culture medium and the cells being cultured can be appropriately maintained.

In addition, due to the use of the roller and the trough-like member, a culture medium or cells being cultured in the culture part are prevented from entering an extensible part (a part other than the culture part of the enclosure part).

For example, as stated in claim 1, when the culture container is placed on the upper surface of the container table, and the roller; is placed thereon, the roller is approximately in line contact with the culture container. On the other hand, when the roller and the trough-like member are used, the roller is approximately in plane contact with the culture container. A culture medium or the like in the culture part can be prevented from entering the extensible part even when the roller is in line contact with the culture container. However, such entering can be prevented more effectively when the roller is in plane contact with the culture container.

The cell culture apparatus of the present invention may have a configuration in which the outer periphery of the cross section in the radial direction of the roller is formed to have a teeth-like structure, and each mountain part and each valley part of this teeth-like structure are formed in a straight line or in a curved line respectively in the axial direction.

Due to such a configuration of the cell culture apparatus, the contact area of the roller and the culture container becomes larger than the case where the roller and the culture container are in line contact, a culture medium or the like in the culture part can be further effectively prevented from entering the extensible part.

The cell culture apparatus of the present invention may have a configuration in which two rollers are provided, and the front and the back of the culture container are held by these rollers so that the enclosure part can be divided into two or more chambers.

Due to such a configuration of the culture apparatus, by holding both surfaces of the culture container by using these two rollers, the culture part of the enclosure part can have an appropriate volume. In addition, by moving the two rollers in the same direction while allowing each roller to rotate, the volume of the culture part can be changed, whereby the cell density of the culture medium and the cells being cultured can be appropriately maintained.

The cell culture apparatus of the present invention may have a configuration in which a pressure applied by the roller to the culture container is 0.1 MPa or more when the roller is placed on the upper surface of the culture container.

Due to such a configuration of the cell culture apparatus, not only a culture medium or the like in the culture part are prevented from entering the extensible part, but also the roller can be moved by rotation.

The cell culture apparatus of the present invention may have a configuration in which the outer peripheral surface of the roller is formed of one or two or more materials selected from urethane rubber, silicone rubber and a thermoplastic resin, and the hardness thereof is at least 90 or less.

Due to such a configuration of the cell culture apparatus, not only a culture medium or the like in the culture part are prevented from entering the extensible part, but also the roller can be moved by rotation.

Furthermore, the cell culture apparatus of the present invention may have a configuration in which it is provided with a holder to remove creases from the culture container placed on the upper surface of the container table.

Due to such a configuration of the cell culture apparatus, the culture part can be extended without generation of creases in the culture container when the roller is rotated.

The cell culture apparatus of the present invention may have a configuration in which it is provided with means for keeping a culture medium and/or cells being cultured enclosed within the culture container 11 uniform.

Examples of such means include a stirring means by which a culture medium or the like in the culture container is stirred. Due to such a configuration of the cell culture apparatus, the culture environment can be uniform, whereby proliferation can be accelerated.

The cell culture system of the present invention may have a configuration in which it comprises a culture medium storage container in which a culture medium is stored; a culture container formed of a soft packing material and in which a culture medium and/or cells being cultured are enclosed; a first tube for supplying a culture medium from the culture medium storage container to the culture container; a harvest container for enclosing the culture medium and/or the cells being cultured which have been harvested from the culture container; and a second tube for supplying the culture medium and/or the cells being cultured from the culture container to the harvest container.

Due to such a configuration of the cell culture system, by providing a tube which connects the cell culture storage container and the culture container, or connects the culture container and the harvest container, it is possible to construct an entirely closed system for the culture medium storage container, the culture container, the harvest container and the gas permissible tube on the one-cassette-per-patient basis. As a result, admixture of various bacteria which occurs in the open system can be eliminated to ensure safety.

Further, the cell culture system of the present invention may have a configuration in which it is provided with a condition-controlling means which, during a period when a culture medium is sent from the culture medium storage container to the culture container, controls one or two or more of the temperature, the amount of dissolved oxygen and the amount of dissolved carbon dioxide of the culture medium to an optimum level.

Due to such a configuration of the cell culture system, a culture medium can be supplied to the culture container with the temperature, the dissolved oxygen amount and the dissolved carbon dioxide amount being in the optimum condition. As a result, cells being cultured can be activated.

The cell culture system of the present invention may have a configuration in which it comprises a container table on which a culture container is placed, a partition member placed on the upper surface of the culture container so as to divide the enclosure part into two or more chambers, and a driving means which moves the partition member and/or the culture container to change the volume of each chamber divided by the partition member, wherein the container table, the partition member and the driving means respectively comprise the container table, the partition member and the driving means according to any one of claims 1 to 10.

Due to such a configuration of the cell culture system, since the movable partition member (for example, a roller) which divides the enclosure part into two or more chambers or the driving means which allows this partition member to move by rotation on the culture container is used, continuous control of the culture volume becomes possible, whereby stabilization of the cell culture environment can be realized. As a result, the proliferation speed, activity or the like of cells can be enhanced.

The cell culture method of the present invention comprising the steps of: placing on the upper surface of the container table a culture container formed of a soft packing material; placing on the upper surface of the thus placed culture container a movable partition member so as to divide an enclosure part of the culture container into two or more chambers; and moving the partition member and/or the culture container by driving a driving means to change the volume of each chamber of the enclosure part.

Due to such a method of cell culture, by moving the partition member such as a roller or the culture container, the volume of a culture part of the culture container in which the culture medium or the cells being cultured is enclosed can be appropriate according to the cell density during the culture.

The cell culture method of the present invention is a method which further comprises the step of moving the partition member towards a tube for harvest which is attached to the culture container; pushing a culture medium and/or cells being cultured enclosed in the enclosure part of the culture container to the tube for harvest, thereby sending the culture medium and/or the cells being cultured to a harvest container connected to the tube for harvest.

Due to such a method of cell culture, automatic harvest of a culture medium or cells being cultured becomes possible.

Advantageous Effects of the Invention

As mentioned above, according to the present invention, not only the culture part of the culture container is divided into two or more chambers by placing a partition member such as a roller on the upper surface of the culture container but also by the rotational movement of this roller on the culture container, the volume of the culture part can be continuously changed, whereby the cell density during the culture can be constantly maintained at an appropriate level.

In addition, since the volume of the culture part can be changed by the rotational movement of the roller, the procedure of transferring cells to another culture container can be eliminated when a large amount of cells are cultured. As a result, admixture of bacteria can be eliminated, damage on cells can be reduced, risk of contamination can be lowered, labor saving can be attained and automation of the process can be realized.

BRIEF DESCRIPTION OF THE DRAWINGS

FIG. 3 is a side view showing the manner of the rotational movement of a single roller, in which (a) is a view showing the rotational movement of a roller during the culture and (b) is a view showing the rotational movement of a roller when harvesting a culture medium or the like;

FIG. 4 is a side view showing the manner of the rotational movement of two rollers, in which (a) is a view showing the rotational movement of rollers during the culture and (b) is a view showing the rotational movement of rollers when harvesting a culture medium or the like;

FIG. 12 is a view showing the program of extended culture in Examples;

FIG. 13 is a view showing the results of culture in Example 1 and Comparative Example 1.

BEST MODE FOR CARRYING OUT THE INVENTION

Preferred embodiments of the cell culture apparatus, the cell culture system and the cell culture method according to the present invention will be explained with reference to the drawings.

[Cell culture apparatus]

First, an embodiment of the cell culture apparatus according to the present invention is explained with reference to FIG. 1.

Figure 1:
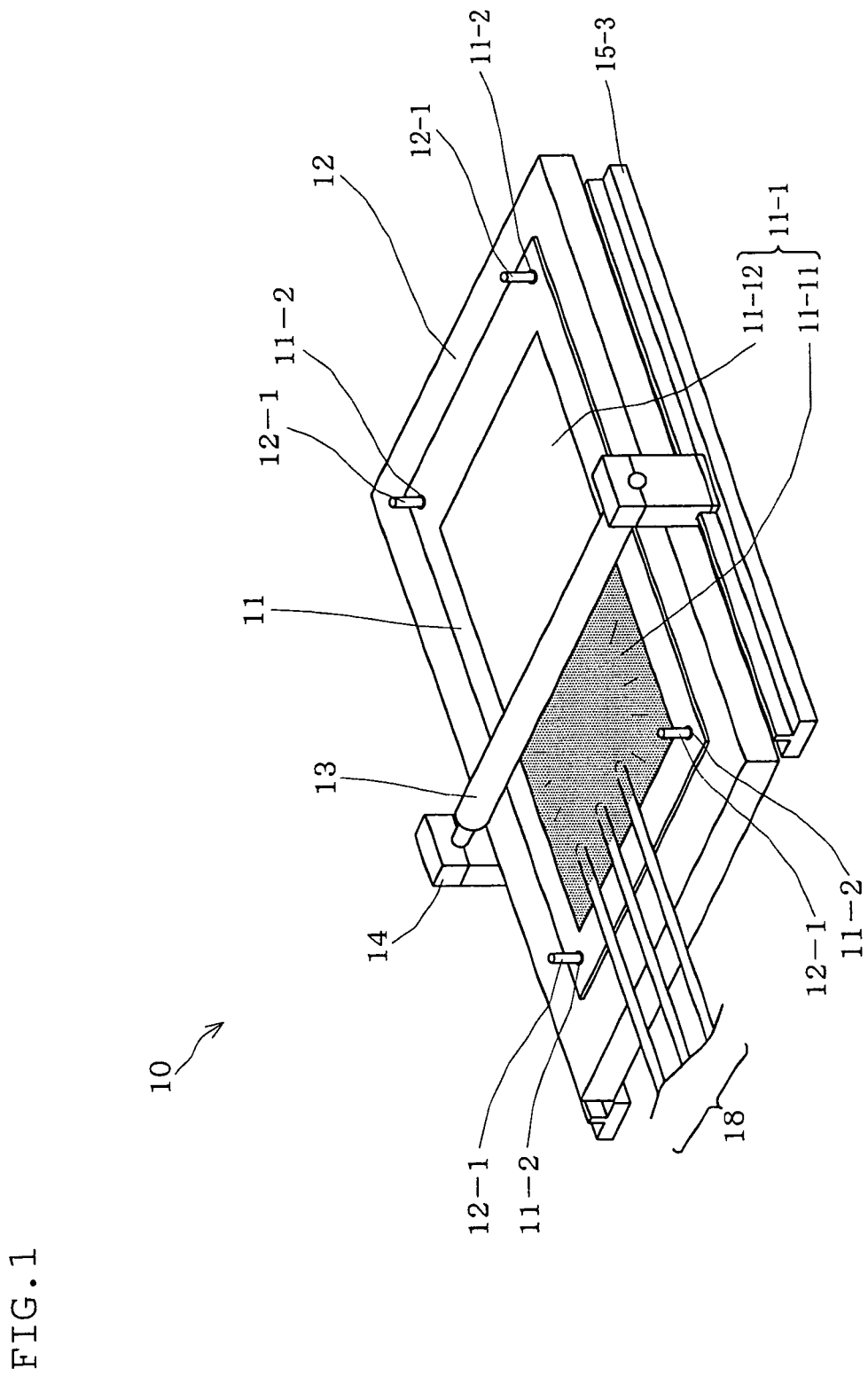
FIG. 1 is an external perspective view showing a configuration of the cell culture apparatus of the present invention.

FIG. 1 is an external perspective view showing the configuration of the cell culture apparatus in this embodiment.

As shown in this figure, a cell culture apparatus 10 is provided with a culture container 11, a container table 12, a roller 13 and a roller-supporting member 14. Furthermore, the cell culture apparatus 10 is provided with a driving means 15, a means 16 for keeping a culture medium and/or cells being cultured enclosed in the culture container 11 uniform, and a measuring means 17.

Here, the culture container 11 is an apparatus in which cells to be cultured (cells being cultured) or a culture medium for culturing the cells are enclosed for culture. This culture container 11 is formed in a bag-like shape (bag type) using a soft packing material as a material.

The soft packing material is a packing material which imparts flexibility and softness to a packing material. Due to the use of the soft packing material, the culture container 11 can flexibly change the volume of a culture part 11-11 by the pressing and rotation of the roller 13. A soft packing material is a well-known technology which is disclosed, for example, in JP-A-2002-255277 (Food Package Using Soft Packaging Film Sheet and Food Taking-Out Method) or in JP-A-2004-323077 (Pressurized Spouting Bag-shaped Container).

In addition, the culture container 11 has gas permeability which is necessary for the culture of cells. Due to this gas permeability, it is possible to allow a cell culture system (mentioned later) to be a closed (enclosed) system. In addition, the culture container 11 is partly or entirely transparent so that the contents thereof can be visibly confirmed.

Specific examples of the packing material satisfying the conditions as the culture container 11 include polyolefins, ethylene-vinyl acetate copolymers, styrene-based elastomers, polyester-based thermoplastic elastomers, silicone-based thermoplastic elastomers and silicone rubber.

In the culture container 11, part which is inherently capable of enclosing cells being cultured or a culture medium is indicated as an enclosure part "11-1", part which becomes capable of enclosing cells being cultured or a culture medium when this enclosure part 11-1 is partitioned by the roller 13 is indicated as a culture part "11-11", and part which inhibits entering of cells being cultured or a culture medium due to the partition by the roller 13 is indicated by an extensible part "11-12" (or a non-culture part "11-12").

Each of the four sides of this culture container 11 is sealed. However, at least two or more tubes 18 are connected thereto. Of these two tubes, one is used for injecting cells being cultured or a culture medium from outside to the culture part 11-11, and the other one is used for harvesting cells being cultured or a culture medium from the culture part 11-11. When three tubes 18 are connected as shown in FIG. 1, the third tube is a sampling tube which is used for taking cells being cultured or a culture medium out of the culture part 11-11 as a sample.

The material of this tube 18 can be appropriately selected according to the environment under which it is used. In particular, it is desirable to use a material improved in gas permeability. Examples thereof include silicone rubber, soft vinyl chloride resins, polybutadiene resins, ethylene-vinyl acetate copolymers, chlorinated polyethylene resins, polyurethane-based thermoplastic elastomers, polyester-based thermoplastic elastomers, silicone-based thermoplastic elastomers and styrene-based elastomers, such as SBS (styrene-butadiene-styrene), SIS (styrene-isoprene-styrene), SEBS (styrene-ethylene-butylene-styrene) and SEPS (styrene-ethylene-propylene-styrene). These are improved in gas permeability.

The container table 12 is a flat table in which the culture container 11 is placed on the upper surface thereof, and the roller 13 is placed on the upper surface of the culture container 11.

On the upper surface of the container table 12, a stop member 12-1 is vertically provided at each of the four corners of part on which the culture container 11 is placed. At each of the four corners of the culture container 11, a hole 11-2 is provided so as to allow the stop member 12-1 to pass therethrough.

By allowing each of the stop members 12-1 to pass through each of the holes 11-2 of the culture container 11, the culture container 11 can be stationary fixed on the upper surface of the container table 12. In addition, shift of the culture container 11 with the move of the roller 13 can be prevented.

The stop member is not limited to the above-mentioned member, and any stop member can be used as long as it has a mechanism which can prevent the culture container 11 from shifting.

In addition, this container table 12 is provided with a means 16 which is used for keeping the uniformity of a culture medium and/or cells being cultured which are accommodated within this container. Details of this means 16 will be mentioned later.

Figure 2:
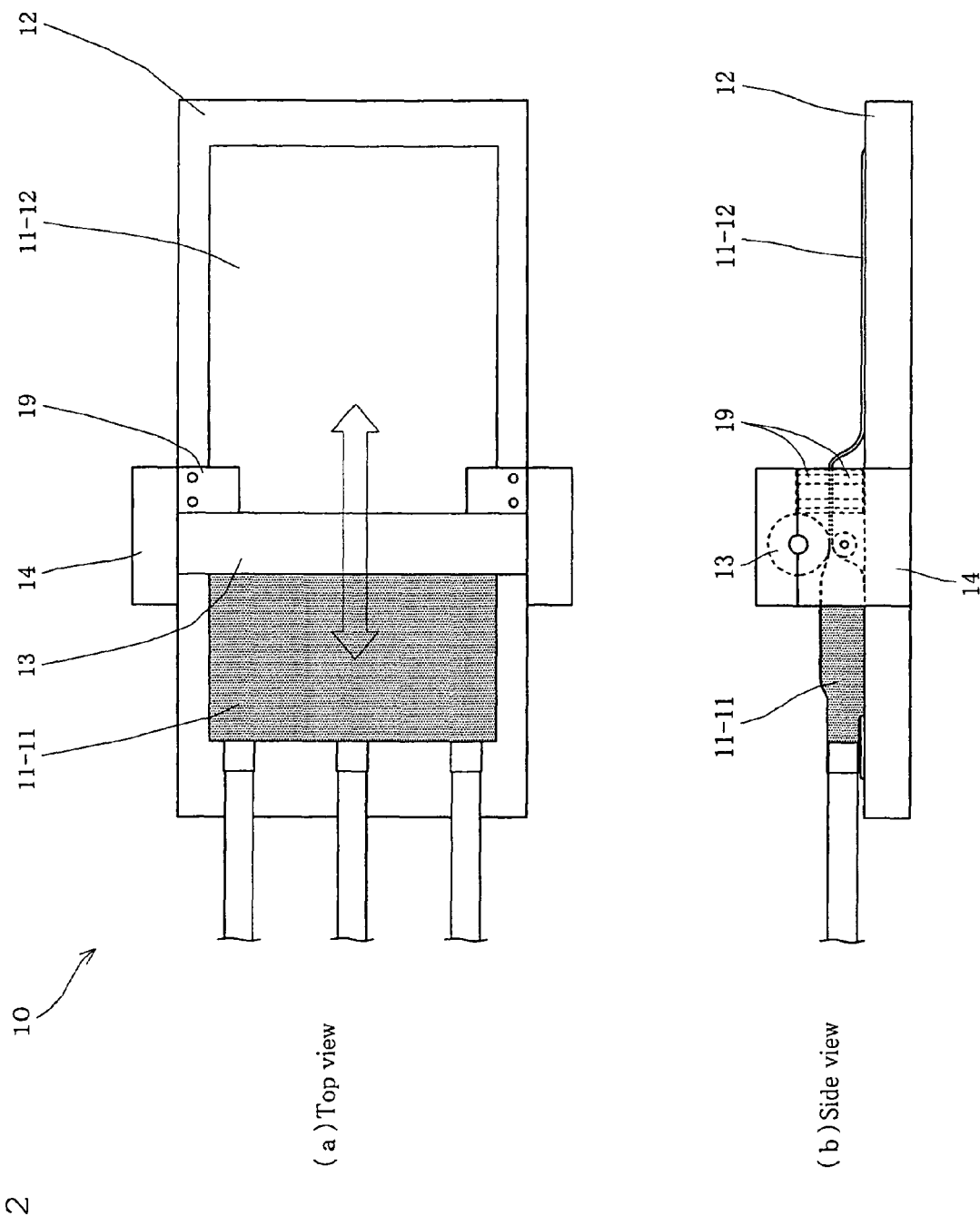
FIG. 2 is a view showing another configuration of the cell culture apparatus of the present invention, in which (a) is a top view and (b) is a side view.

Further, as shown in FIGS. 2(*a*) and (*b*), a holding member 19 is provided on the surface of the container table 12 to prevent generation of creases on the surface of the culture container 11.

The holding member 19 is provided in a roller-supporting member 14, and has a mechanism of being capable of moving while holding the two sides of the culture container 11 in the extensible part 11-12.

Due to the provision of the holding member 19, the culture part 11-11 can be extended without generation of creases in the culture container 11 when the roller 13 moves.

The shape of the holding member 19 is not limited to that mentioned above, and any holding member can be used as long as it has a mechanism of guiding part of the culture container 11 and preventing the culture container 11 from entering obliquely relative to the roller 13.

In this embodiment, a roller is used as a movable partition member. The roller 13 is formed to have a cylindrical shape, and arranged on the upper surface of the culture container 11 such that the axial direction thereof becomes parallel with the width direction of the culture container 11. As shown in FIG. 1, it is allowed to move horizontally along the longitudinal direction of the culture container 11.

The length in the axial direction of this roller 13 is set such that is becomes longer than the width of the cell culture container 11 (or the width of the enclosure part 11-1).

In addition, the roller 13 has a mechanism in which the surface of the roller 13 pushes the culture container 11 by the self weight thereof (or by a powering means (not shown) in the roller-supporting member 14)).

Due to such a configuration, the enclosure part 11-1 of the culture container 11 is divided into two chambers, i.e. the culture part 11-11 and the extensible part 11-12, with a portion which is pressed by the roller 13 being a boundary. In this case, a part provided on the side to which the tube 18 linking to a culture medium storage container 20 (mentioned later) is connected serves as the culture part 11-11, in which cells being cultured or a culture medium are enclosed.

When the roller 13 moves by rotation in the longitudinal direction of the culture container 11 while being in contact with the upper surface of the container, the volume of the culture part 11-11 is allowed to change continuously.

Figure 3:
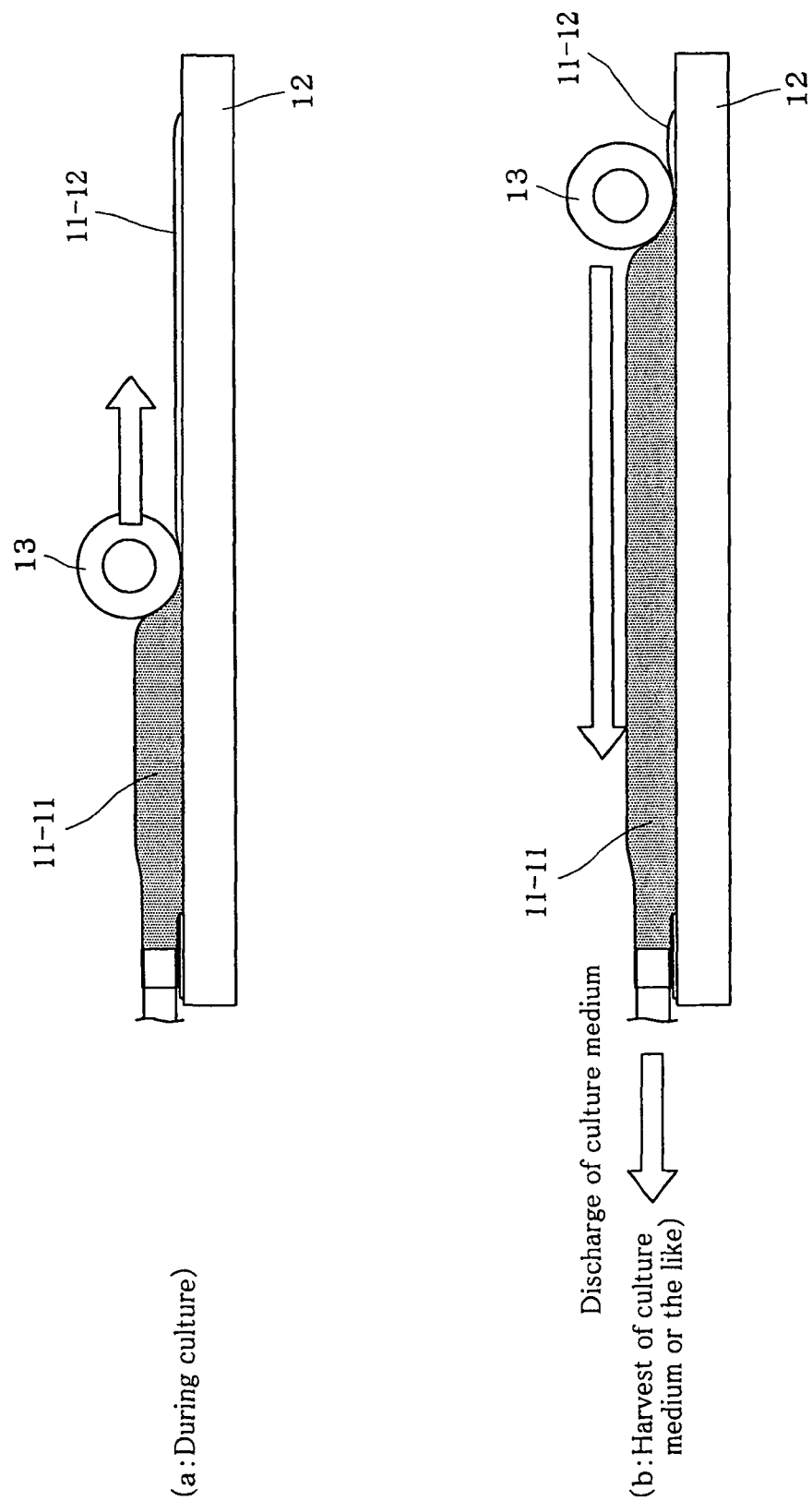

Specifically, as shown in FIG. 3(*a*), when the cells are being cultured in the container part 11-11, the roller 13 is controlled so as to move in a direction in which the volume of the culture part 11-11 is increased. As a result, the volume of the culture part 11-11 can be kept at an optimum level according to the culture status.

On the other hand, when a culture medium or cells being cultured are harvested after the completion of the culture, as shown in FIG. 3(*b*), the roller 13 moves in a direction in which the volume of the culture part 11-11 is reduced. As a result, a culture medium or cells being cultured which have been pressed by means of the roller 13 are pushed outside (for example, in a harvest container 50 (mentioned later)) through the tube 18, whereby they can be automatically harvested.

Meanwhile, in this embodiment, a moving means which controls the movement of the roller 13 as mentioned above comprises a roller-supporting member 14 and a driving means 15, which will be mentioned later (see FIG. 7).

As the surface material forming the outer peripheral surface of the roller 13, one or two or more material selected from urethane rubber, silicone rubber and a thermoplastic resin can be used, for example.

The hardness of this surface material is at least A90 or smaller (JIS K 6253).

Here, the hardness 90 is A90, which is measured by means of a durometer (Type A) in accordance with JIS K 6253.

By using a material having such a hardness, culture can be conducted without the fear that the culture container 11 is damaged and a culture medium and cells being cultured, which are charged in the culture part 11-11, are leaked to the extensible part 11-12.

In FIG. 1, only one roller 13 is provided. However, the number of the roller is not limited to one, and a plurality of rollers may be provided.

Figure 4:
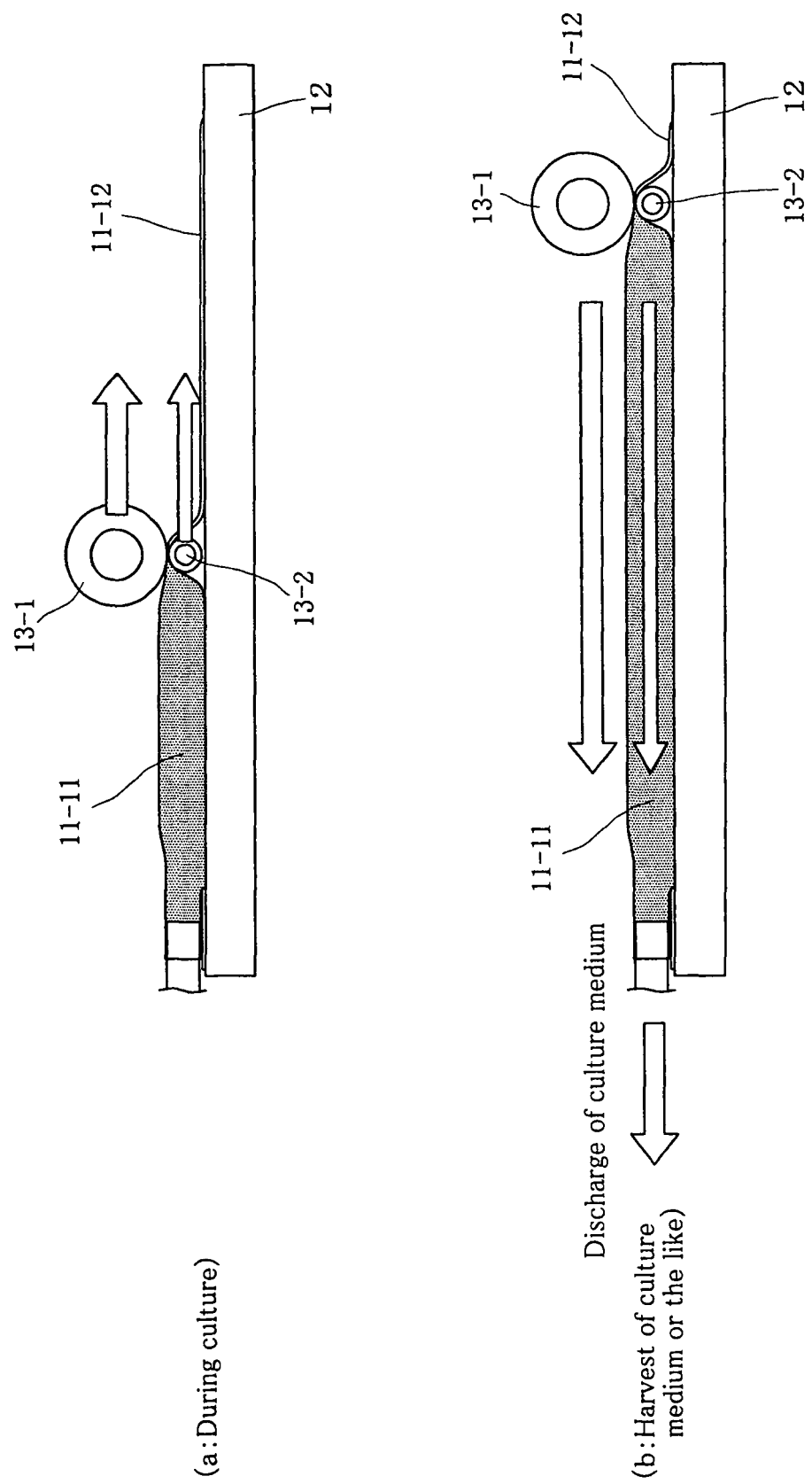

For example, as shown in FIGS. 4(*a*) and (*b*), two rollers 13 are provided and arranged one on another, whereby the culture container 11 is passed between these rollers (the first roller 13-1 and the second roller 13-2). Due to such a configuration, at a part which is held between the roller 13-1 and the roller 13-2, the enclosure part 11-1 of the culture container 11 can be divided into the culture part 11-11 and the extensible part 11-12.

By moving (rotating) the rollers 13-1 and 13-2 in the longitudinal direction of the cell culture container 11 in the same direction, the volume of the culture part 11-11 of the culture container 11 can be continuously changed. For example, when cells are cultured in the culture part 11-11, as shown in FIG. 4(a), the rollers can be moved in a direction in which the volume of the culture part 11-11 is increased. As a result, a volume which is appropriate for the culture can be maintained. On the other hand, when a culture medium or cells being cultured are harvested after the completion of the culture, as shown in FIG. 4(b), the rollers move in a direction in which the volume of the culture part 11-11 is reduced, whereby the culture medium or the like can be automatically harvested.

As shown in FIGS. 5(a) and 5(b), in the roller 13, a trough-like member 13-3 may be provided along the outside (the lower side in these figures) of the outer periphery of the roller 13.

The trough-like member 13-3 is a member having the shape of a trough with an arc-shaped cross section, which is formed along the outer periphery of the roller 13. Specifically, the trough-like member 13-3 is formed such that the arc of the trough-like member 13-3 and the outer peripheral circumference of the roller 13 become almost concentric, whereby the roller 13 is accommodated within the trough-like member 13-3.

In addition, this trough-like member 13-3 is allowed to move horizontally along the longitudinal direction of the culture container 11 with the above-mentioned rotational movement of the roller 13. Specifically, since the both ends of the trough-like container 13-3 are held by a roller-supporting member 14, the trough-like container 13-3 moves horizontally above the container table 12 with the horizontal movement of the roller 13 caused by the roller-supporting member 14.

Figure 5:
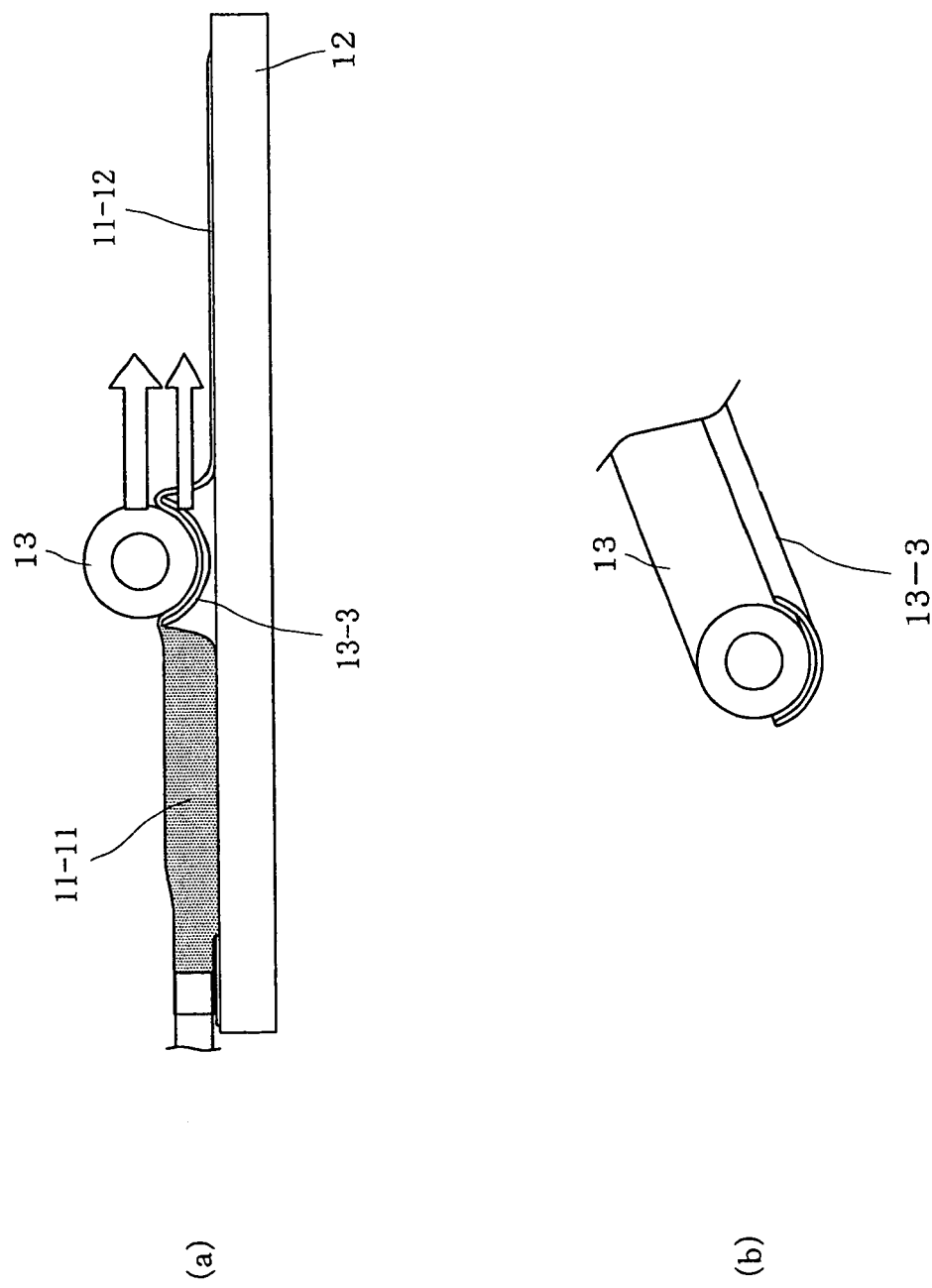
FIG. 5 is a view showing a state in which a trough-like member is provided, in which (a) is a side view of the cell culture apparatus and (b) is a perspective view of a roller and a trough-like member.

By providing the culture container 11 between the trough-like 13-3 and the outer periphery of the roller 13 such that the culture container 11 is passed therebetween, as shown in FIG. 5, the culture container 11 becomes curved along the inner surface of the trough-like member 13-3 (the outer periphery of the roller 13), whereby it is held between the roller 13 and the trough-like member 13-3.

The culture container 11 is held between the roller 13 and the trough-like member 13-3, and the curved portion thereof is adhered to the outer periphery of the roller 13. As a result, the roller 13 is not in line contact with, but in plane contact with the culture container 11, and the sealing performance in this portion improves, whereby cells being cultured or a culture medium can be prevented from moving from the culture part 11-11 to the extensible part 11-12 more surely.

Also in such a configuration, as in the case shown in FIG. 3 or 4, the volume of the culture part 11 of the culture container 11 can be continuously changed.

Figure 6:
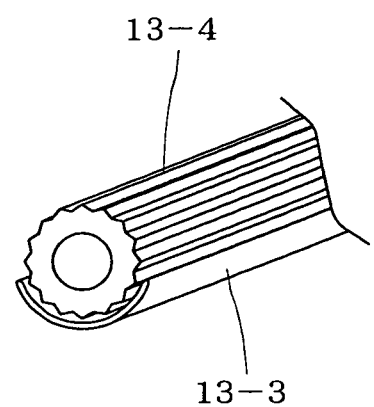
FIG. 6 is a perspective view showing the structure of a serrated roller.

As shown in FIG. 6, the roller 13 can be a serrated roller 13-4, in which the outer periphery of the cross section in the radial direction thereof has a teeth-like structure. In this roller 13-4, each mountain part and each valley part are formed in a straight line or in a curved line respectively in the axial direction of the roller. Here, the expression "formed in a straight line" means that the mountain part and the valley part are in the same positions in every radial cross section. On the other hand, the expression "formed in a curved line" means that the mountain part or the valley part is curvedly formed in the outer peripheral surface of the roller 13-4. In this case, in a plurality of radial cross sections, the positions of the mountain part and the valley part differ from each other.

As shown in FIG. 6, the trough-like member 13-3 is formed outside the outer periphery of the roller 13-4. Due to such a configuration, the contact area of the outer periphery of the roller 13-4 and the culture container 11 is increased as compared with the case shown in FIGS. 3 and 4, whereby cells being cultured or a culture medium are prevented from being moved from the culture part 11-11 to the extensible part 11-12.

Further, as in the case of FIG. 5(a), by moving the roller 13-4 and the trough-like member 13-3 in the same direction (the roller 13-4 moves by rotation), the volume of the culture part 11-11 of the culture container 11 can be changed continuously. As a result, the volume suitable for the culture can be maintained, and a culture medium or cells being cultured can be automatically harvested.

It is preferred that the tip of the mountain part of the teeth-like structure be rounded such that no scratch is made on the culture container 11.

The roller-supporting member 14 is a moving means which allows the roller 13 to move in the horizontal direction while holding the roller 13.

Specifically, as shown in FIG. 1, the roller-supporting member 14 are provided vertically and upwardly on the both sides of the container table 12 such that one supporting means is provided on each side. The roller-supporting members 14 are respectively connected to the end portion of the roller 13 to support the roller 13. That is, the both end portions of the roller 13 are attached to the roller-supporting member 14, and the roller 13 is supported by the roller-supporting member 14.

When the roller-supporting member 14 is driven by a driving means 15, the roller 13 moves horizontally above the container table 12, whereby the volume of the culture container 11 can be changed continuously.

Specifically, in this embodiment, the roller-supporting member 14 is divided into a body part 14-1 and a lid part 14-2. On each of the upper surface of the body part 14-1 and the lower surface of the lid part 14-2, a recess (not shown) for accommodating a bearing which has been fitted to the end portion of the roller 13 is formed. Due to such a configuration, the roller 13 can be taken out by removing the lid part 14-2. In addition, in the state where the roller 13 is removed, it is possible to place the culture container 11 on the upper surface of the container table 12, or to remove the culture container 11.

The driving means 15 is a driving part for moving the roller-supporting member 14 in the horizontal direction.

Figure 7:
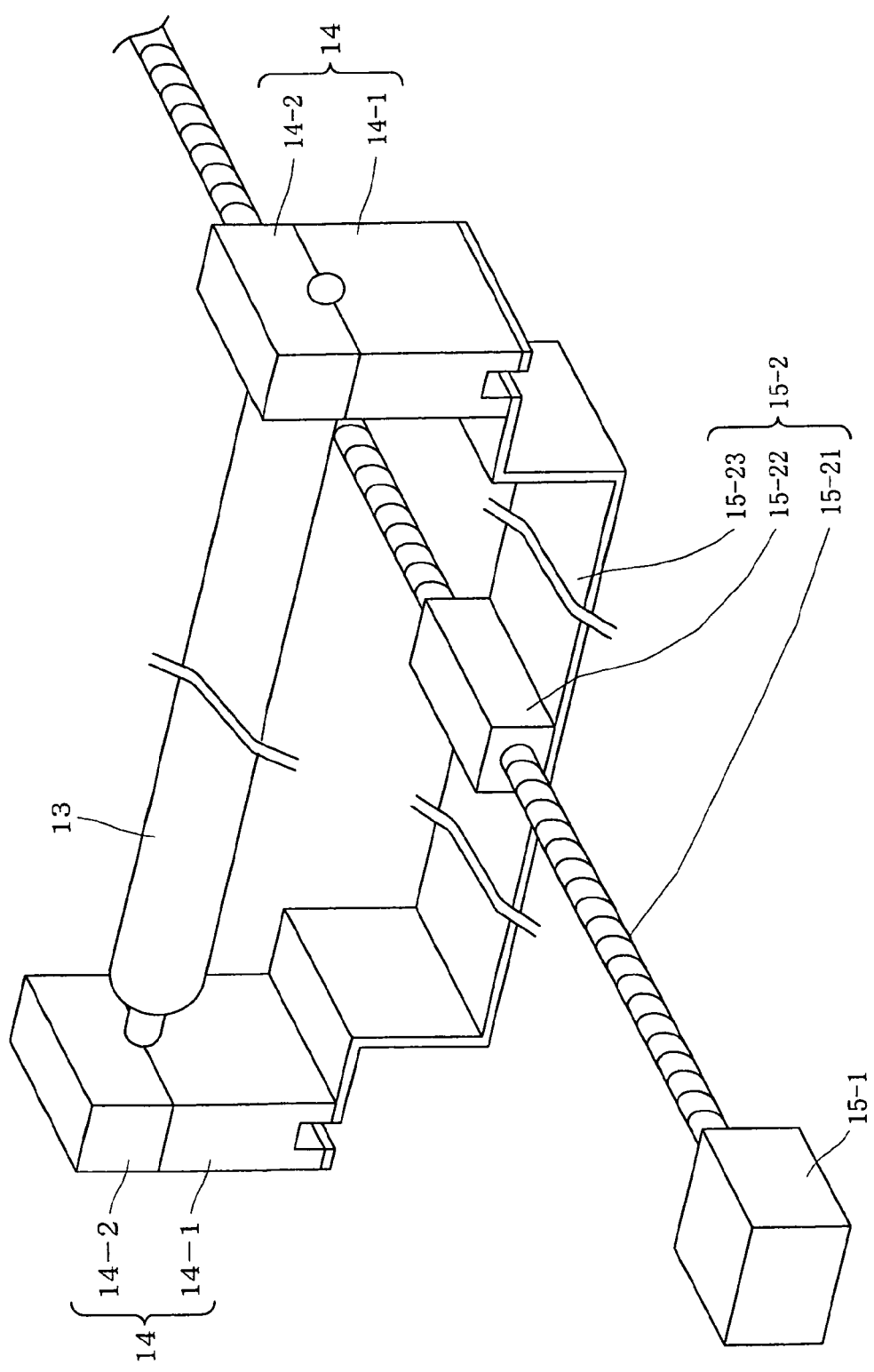
FIG. 7 is a perspective view showing the structure of the driving means.

As shown in FIG. 7, in this embodiment, this driving means 15 is provided with a power-generating means 15-1, a power-transmitting member 15-2 which transmits the power generated in the power in this power-generating means 15-1 to the roller-supporting member 14, and a rail 15-3 on which the roller-supporting member 14 is placed (see FIG. 1).

The power-generating means 15-1 is a means which generates motions such as a rotational movement or a piston movement. A stepping motor can be used as the power-generating means 15-1, for example. A stepping motor is suitable as the power-generating means 15-1 in the present invention since the revolution or rotation angle can be easily controlled.

The power-transmitting member 15-2 transmits power generated in the power-generating means 15-1 to the roller-supporting member 14 such that the power generated in the power-generating means 15-1 allows the roller-supporting member 14 to move horizontally.

For example, as shown in FIG. 7, if the power-generating means 15-1 is a stepping motor, the power-generating means 15-2 is provided with a rod-like screw member 15-21 which is directly connected to the axis of the stepping motor and rotates with the rotation of the axis, and a rotation-receiving member 15-22 which is provided with a threaded part fitted to threads formed on the outer periphery of the rod-like screw member 15-21 and moves in the axial direction of the rod-like screw member 15-21 with the rotation of the rod-like screw member 15-21, and a movement-transmission member 15-23 which connects this rotation-receiving member 15-22 and the roller-supporting member 14 to transmit the horizontal movement of the rotation-receiving member 15-22 to the roller-supporting member 14.

The configuration of the driving means 15 is not limited to one shown in FIG. 1 or FIG. 7, and any preferable, known configuration can be used.

If the number of the roller 13 is plural or the roller 13 is provided with the trough-like member 13-3, they can be moved horizontally (the roller 13 can be moved by rotation) by connecting the roller 13 or the trough-like member 13-3 to the roller-supporting member 14 with the mechanism shown in FIG. 7.

In the explanation given above, description was made on a configuration in which the roller 13 is moved by rotation on the upper surface of the culture container 11 to allow the volume of the culture part 11-11 to change. The change in volume of the culture part 11-11 can be realized by the relative movement of the roller 13 and the culture container 11. Accordingly, the volume of the culture part 11-11 of the culture container 11 can be changed also by fixing the position of the roller 13 or the roller-supporting member 14 and moving the culture container 11 or the container table 12 in the horizontal direction, for example.

The mechanism in which the container table 12 is allowed to move in the horizontal direction can be realized by a configuration similar to that shown in FIG. 7, in which the roller-supporting member 14 is moved horizontally.

As for the configuration of the means 16 for keeping the culture medium and/or the cells being cultured which are enclosed in the culture container 11 uniform, it may be a means capable of shaking or the like of the container table 12, and the examples of which include the following:
a) a means which allows the container table 12 to advance straightwardly, rotate or move on the same plane as that of the means;
b) a means which allows the container table 12 to move like a seesaw;
c) a means which allows the container table 12 to swing at a fixed or a plurality of angles relative to the same plane;
d) a means which allows the container table 12 upside down;
e) a means which has a mechanism capable of stirring a culture medium and cells being cultured within the culture container 11 by allowing the roller 13, a roller with an irregular surface or the like to move between the container table 12 and the lower surface of the culture container 11;
f) a means which has a mechanism capable of stirring a culture medium or cells being cultured within the culture container 11 by pushing up or pressing a plurality of locations of the lower surface or the upper surface of the culture container 11 (both upper and lower surfaces may be pushed up or pressed); and
g) a means having at least one of the above mentioned mechanisms.

Specifically, the means 16 has a mechanism in which a roller is allowed to move by rotation reciprocally and horizontally along the longitudinal direction of the culture container between the container table 12 and the lower surface of the culture container 11. This roller is different from the roller 13. This roller moves by rotation reciprocally the culture part 11-11, in a range extending from the side at which the tube 18 is attached to the roller 13. Due to the reciprocal movement of this roller, cells being cultured and a culture medium in the culture part 11-11 are stirred and homogenized. Further, this roller has a mechanism that the reciprocation distance is changed with the move of the roller 13, whereby a culture medium and or cells being cultured which are enclosed in the culture part 11-11 can always be kept uniform.

The measuring means 17 is a means for measuring the condition of cells being cultured or a culture medium. The position of the roller 13 is determined based on the measurement results of the measuring means 17.

As for the configuration of the measuring means 17, a means provided with a mechanism capable of observing cells in the enclosure part 11-1 of the culture container 11 by means of a CCD camera, a means provided with a mechanism capable of sampling part of a culture medium and cells being cultured in the culture part or the like can be given.

[Shape of the Enclosure Part of the Culture Container]

The shape of the enclosure part 11-1 of the culture container 11 is generally rectangular (see FIG. 1).

However, a rectangular shape is inconvenience when the volume of the culture part 11-11 is required to be reduced. For example, if the roller 13 is moved by rotation to the vicinity of the tube 18, the culture part 11-11 becomes longer and narrower in the width direction of the culture container 11, and becomes unsuitable for culture. In addition, since the roller 13 cannot be moved in a part where the tube 18 is attached, no further reduction in the culture part cannot be attained.

The shape of the enclosure part 11-1 is changed to a shape which becomes gradually narrower towards a part at which the tube 18 is attached. Specifically, the shapes shown in FIGS. 8(*a*) to (*d*) can be used.

Figure 8:
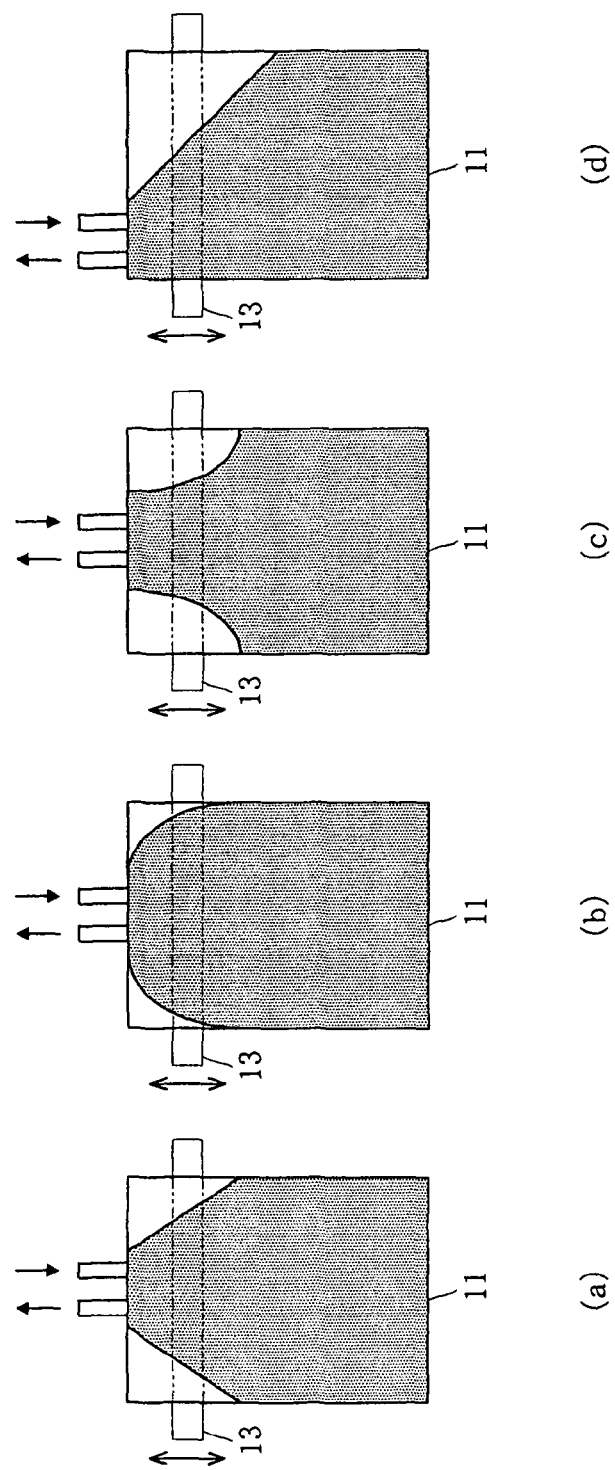
FIG. 8 is an elevation view showing an example of the shape of an enclosure part of the culture container.

For example, as shown in FIG. 8(*a*), the margin part on the right or left shoulder of the culture container 11 is allowed to have a right-angle triangle shape, allowing the oblique side of the shoulder of the enclosure part 11-1 to be linear.

In addition, as shown in FIGS. 8(*b*) and (*c*), the oblique side of the margin part on each shoulder of the culture container 11 can be curved, like a convex or a concave.

Further, as shown in FIG. 8(*d*), the tube 18 may be attached not to the center of a side of the culture container 11 but to the vicinity of one of the corners, whereby the shape of a margin at another corner can be a right-angle triangle and the oblique side of the shoulder of the enclosure part 11-1 can be linear.

Due to such a configuration, as shown in FIGS. 8(*a*) to (*d*), even when the roller 13 is moved by rotation to the vicinity of the tube 18, the culture part 11-11 is prevented from being longer and narrower, and the culture part 11-11 can be wide to some extent from side to side and front and rear. As a result, the culture environment can be kept appropriately, whereby proliferation can be accelerated.

[Cell Culture System]

Then, an embodiment of the cell culture system is explained with reference to FIG. 9.

Figure 9:
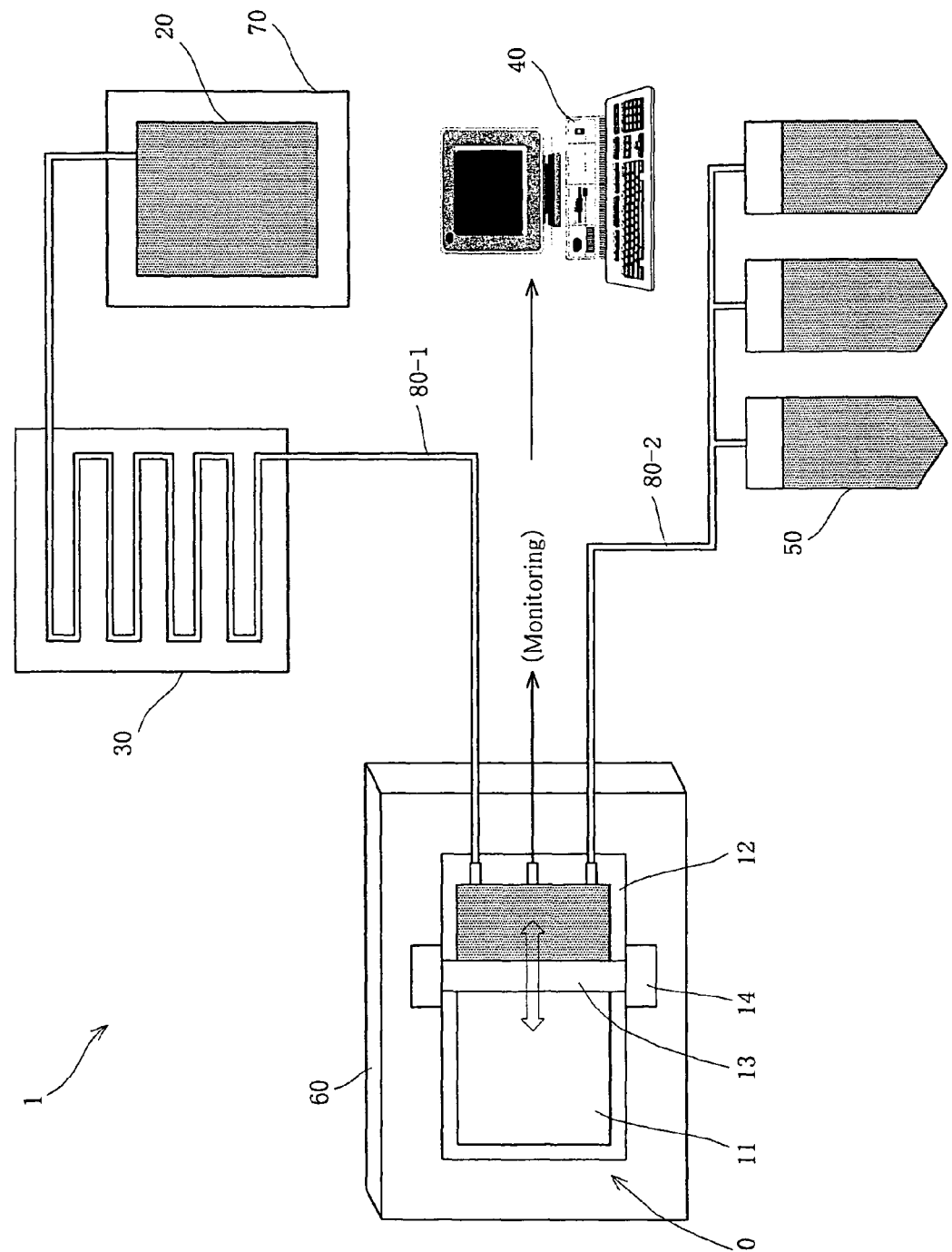
FIG. 9 is a view showing the configuration of the cell culture system.

FIG. 9 is a schematic view showing the configuration of the cell culture system.

As shown in FIG. 9, a cell culture system 1 is provided with the cell culture apparatus 10, a culture medium storage container 20, a heating/gas controlling part 30, a monitoring apparatus 40 and a harvest container 50.

The cell culture apparatus 10 has a configuration similar to the cell culture apparatus 10 shown in FIG. 1. This cell culture apparatus 10 is accommodated within an incubator (thermostatic chamber) 60. In this incubator 60, the temperature, oxygen concentration and carbon dioxide concentration can be controlled. For example, control can be conducted such that the temperature, the oxygen concentration and the carbon dioxide concentration become 37° C., 20% and 5%, respectively, whereby a stable culture environment can be ensured.

The culture medium storage container (culture medium tank) 20 is a container for keeping a culture medium before injection to the culture container 11. This culture medium storage container 20 is accommodated within a storage device (cooler) 70.

This culture medium storage container 20 and the culture container 11 (placed on the container table 12) are connected by means of a flexible tube 80-1. When the volume of the culture part is increased, a culture medium is sent from the culture medium storage container 20 to the culture container 11. The material of the tube 80-1 may be the same as that of the tube 18 in FIG: 1.

In the heating/gas controlling part (condition adjusting means) 30, a culture medium kept cool is heated to a required temperature. In addition, the amount of dissolved oxygen, the amount of dissolved carbon dioxide and pH of a culture medium are controlled.

Due to such a mechanism, lowering in temperature of the culture part can be prevented when supplying a culture medium. In addition, the amount of dissolved oxygen, the amount of dissolved carbon dioxide and pH of a culture medium can be improved to an optimum level.

The monitoring apparatus 40 monitors the cell density, the amount of dissolved oxygen, the amount of dissolved carbon dioxide and pH of a culture medium, which are obtained by analyzing an image measured by said measuring means 17 or by measuring a sampled culture medium, and based on the results obtained, controls the volume of the culture part 11-11, whereby the amount of a culture medium to be supplied to the culture part 11-11, the amount of dissolved oxygen, the amount of dissolved carbon dioxide and pH are controlled. Due to these mechanisms, it becomes possible to keep a culture medium and cells in the culture part 11-11 at an optimum level, whereby a stable culture environment can be ensured.

The harvest container (a bottle for centrifugation) 50 is a container for putting cells being cultured or a culture medium which have been harvested from the culture container 11.

This harvest container 50 can be attached to a centrifugal separator, whereby cells being cultured can be harvested while maintaining the closed system, and the cells being cultured are harvested from a culture medium by centrifugation.

The harvest container 50 and the culture container 11 (placed on the container table 12) may be connected by means of a flexible tube 80-2. A culture medium and cells being cultured are harvested from the culture container 11 to the harvest container 50 through this tube 80-2.

Figure 10:
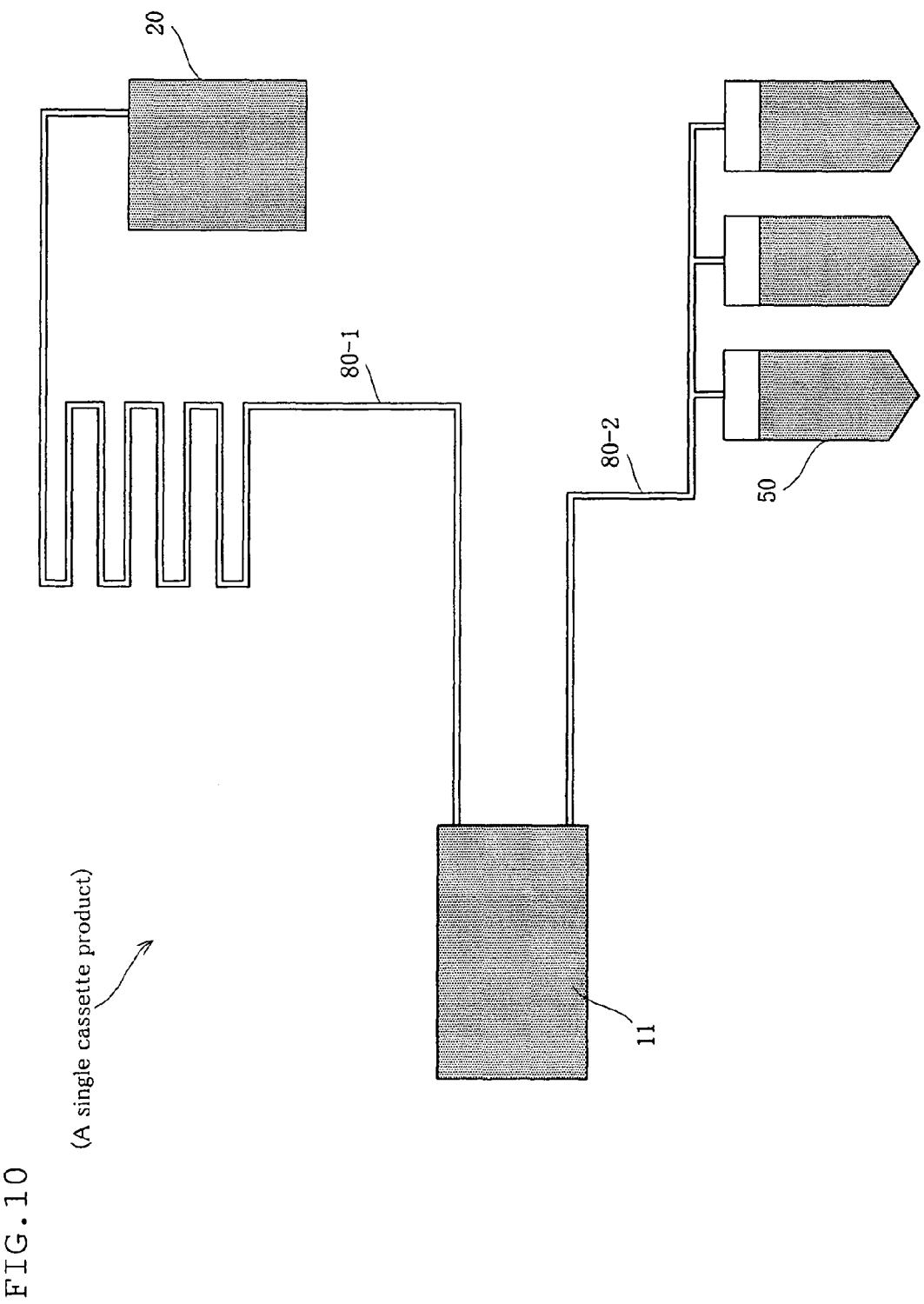
FIG. 10 is a view showing the configuration in which the culture medium storage container, the culture container, the harvest container and the tube are made into a single cassette product.

Further, as shown in FIG. 10, the culture medium storage container 20, the culture container 11, the harvest container 50 and the tube 80 can be used as a single cassette product. That is, these apparatuses are made into an entirely-closed system, and is provided such that one patient uses a single cassette. As a result, enter of various bacteria or cross contamination can be eliminated, and safety can be ensured.

[Operation of Cell Culture Apparatus]

Next, operation of the cell culture apparatus (cell culture method) in this embodiment will be explained.

(Volume Control of the Culture Part by Means of a Roller)

For example, during culture, the roller 13 is provided at a position which makes the volume of the culture part 11-11 appropriate according to the amount of cells and the cell density. Then, the roller 13 is allowed to move in accordance with the amount of cells or the passage of time. Finally, the roller 13 is moved to a position so that almost all of the enclosure part 11-1 becomes an enclosure space.

When a culture medium or cells being cultured are harvested, the roller 13 is allowed to move by rotation towards a side at which the tube 18, which is linked to the harvest container 50, is connected. As a result, the volume of the culture part 11-11 is reduced, and a culture medium or the like is harvested to the harvest container 50 through the tube 18 (discharge of a culture medium or the like).

(Volume Control of the Culture Part Based on the Measurement Results)

As for the volume control of the culture part based on the measurement results, it becomes possible to continue culture under an optimum environment by measuring the number of cells per area of the culture part 11-11 by using a CCD camera, and, based on the results, by adding a culture medium such that the number of cells being cultured in the culture part 11-11 is within a predetermined range.

As mentioned above, according to the cell culture apparatus, the cell culture system and the cell culture method in this embodiment, due to a configuration in which the roller is placed on the upper surface of the culture container so as to divide the culture part into two or more chambers and the volume of the culture part is changed by allowing the roller to move by rotation, culture can be possible in a single culture container, and automation of culture can be realized.

Due to such a configuration, the need of subculture is eliminated, thus significantly lowering the risk of being contaminated by germs or the like.

In addition, since the culture volume can be successively controlled, the cell culture environment can be stabilized. Therefore, the proliferation speed, activity or the like of cells can be enhanced.

EXAMPLES

Example 1

Figure 11:
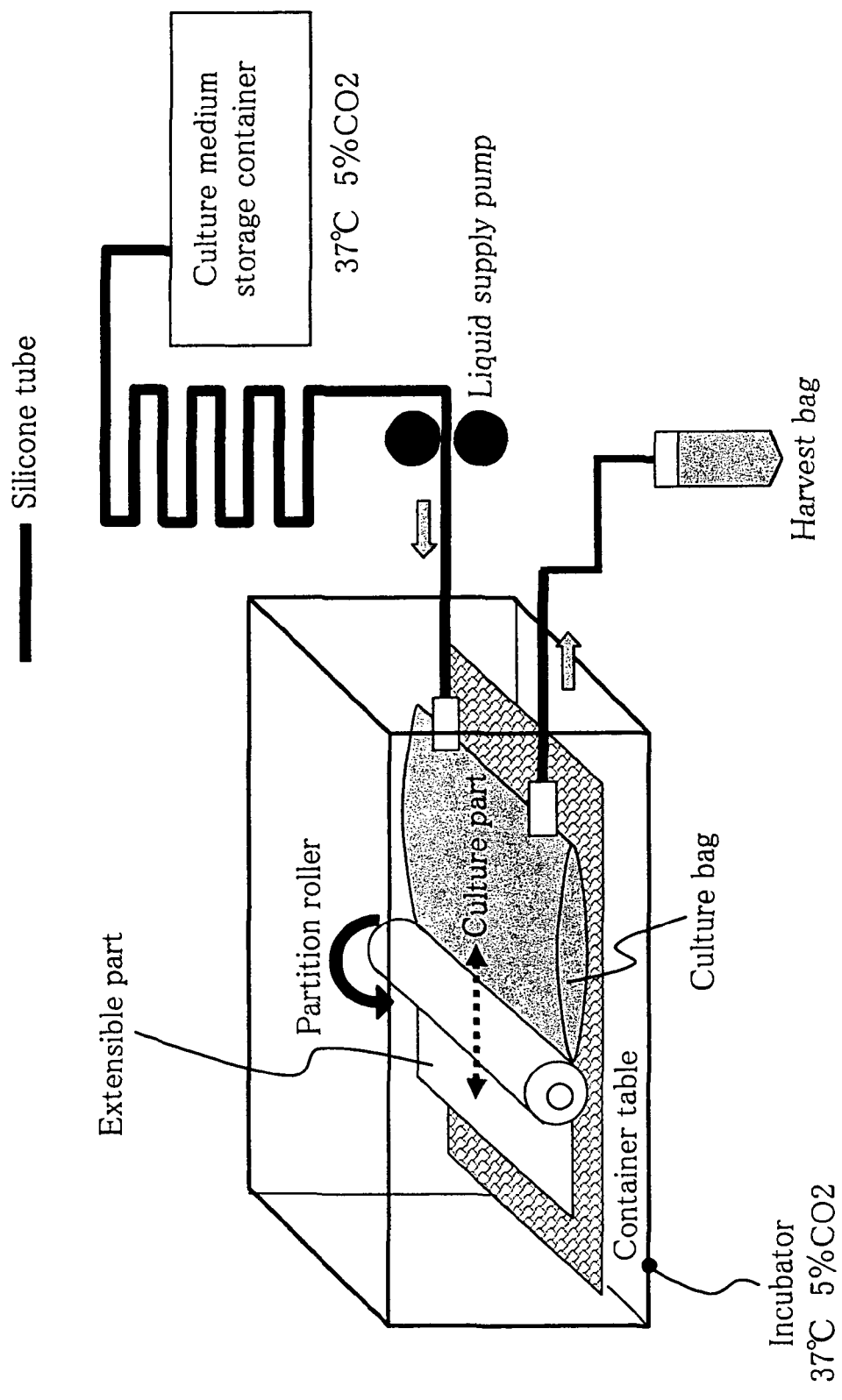
FIG. 11 is a view showing a schematic configuration of the cell culture apparatus used in Examples.
Figure 14:
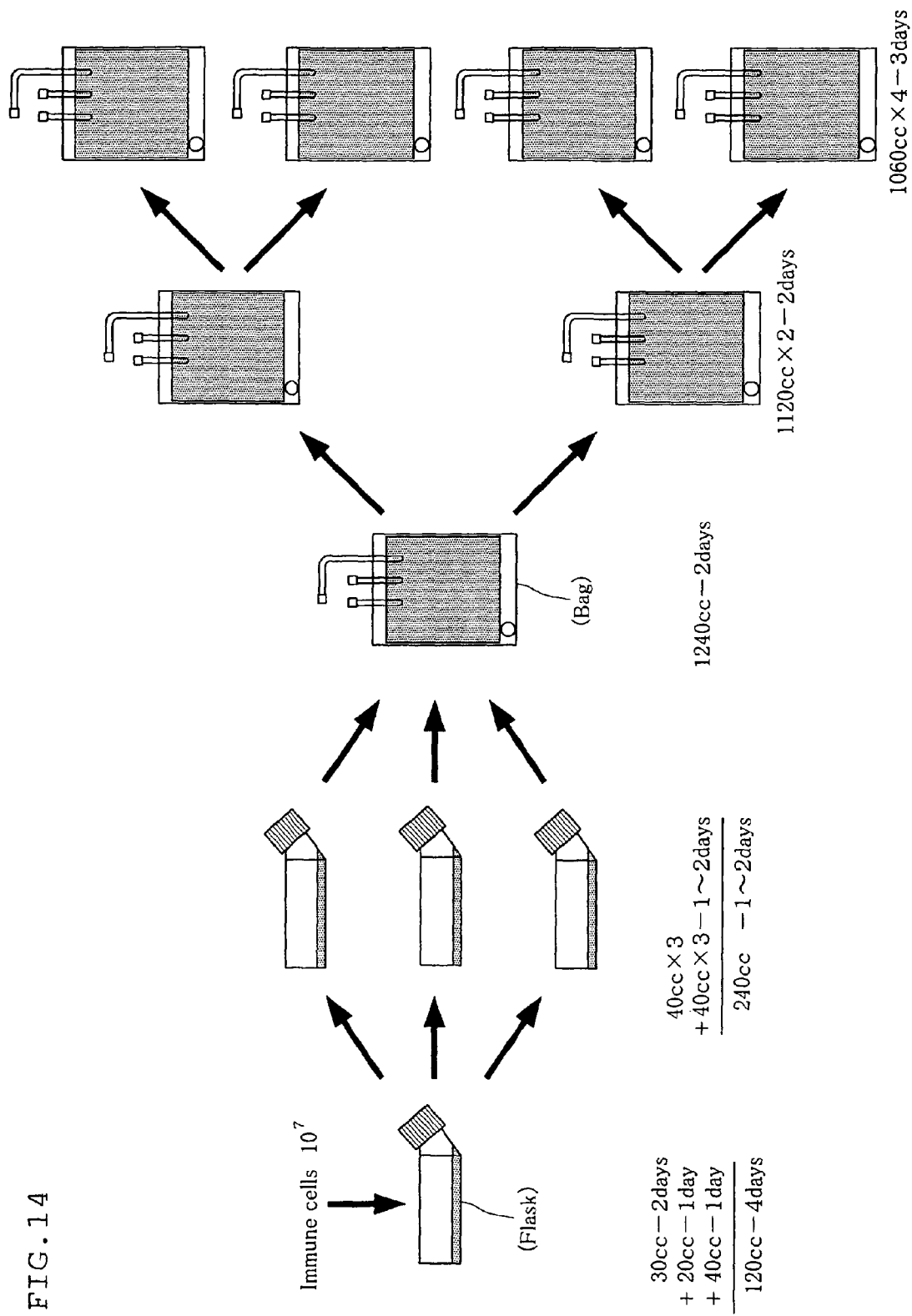
FIG. 14 is a view showing the conventional procedure of subculture.

As shown in FIG. 11, a cell culture test was conducted by using the cell culture apparatus of the present invention. As the culture bag, a 172×250 mm polyethylene-made culture bag was used. The culture medium storage container was charged with 500 ml of RPMI1640 (invitrogen), and then allowed to stand under an atmosphere of 37° C.-5% $CO_2$. Then, this culture bag was connected to this culture medium storage container through a silicone tube.

The culture bag placed on the container table was pressed by a partition roller (the outer peripheral surface thereof was made of silicone: rubber hardness, 70) from above, whereby the enclosure part of the culture bag was divided into two chambers, i.e. a culture part and an extensible part. The pressure applied by the partition roller was 0.12 MPa.

At this time, the position of the partition roller was set such that the area of the culture part at the time of starting culture became 120.4 $cm^2$ (172×70 mm). Then, by using a medium supply pump, 100 ml of a culture medium was supplied from the culture medium storage container to the culture part of the culture bag. At the same time, $1.0×10^7$ Jurkat cells, human T-cell leukemia cells, were enclosed and culture was initiated. The culture was conducted under an atmosphere of 37° C.-5% $CO_2$.

Then, as shown in FIG. 12, with a predetermined time interval, the partition roller was moved in the direction of the extensible part, whereby the area (volume) of culture part was gradually increased, and a culture medium was supplied from the culture medium storage container.

As mentioned above, a culture medium was supplied from the culture medium storage container with an extension of the culture part. Finally, the culture part was extended to the maximum size (172×250 mm), the amount of a culture medium was increased to 500 ml, and culture was conducted.

After the lapse of 120 hours, the cells were harvested from the culture part, and the number of the cells was counted. The number of the cells was $4.3 \times 10^8$. The results are shown in FIG. 13.

Comparative Example 1

Using the same culture bag as that used in Example 1, the culture was conducted without gradually increasing the area of the culture part.

Specifically, in Comparative Example 1, the culture bag was not divided into two chambers by means of the partition roller. The entire enclosure part of the culture bag was used, and culture was conducted with the culture part area and the culture medium amount being 430 $cm^2$ and 500 ml, respectively, from the start of the culture.

The cells used were Jurkat cells (human T-cell leukemia cells) as in Example 1. The quantity of the cells was $1.0 \times 10^7$. The culture was conducted under an atmosphere of 37° C.-5% $CO_2$.

After the lapse of 120 hours, the cells were harvested from the culture part, and the number of the cells was counted. The number of the cells was $3.3 \times 10^8$. The results are shown in FIG. 13.

As shown in FIG. 13, as in Example 1, when the culture part was extended with the proliferation of the cells to appropriately control the density of the cells being cultured, the number of cells was increased by 43 times after the lapse of 120 hours.

In contrast, as in Comparative Example 1, when all of the culture medium was put in the enclosure part of the culture bag to conduct culture, the number of cells was increased by 33 times after the lapse of 120 hours.

From the above results, it becomes apparent that a higher degree of cell proliferation effects can be attained by controlling the cell density in accordance with the proliferation of cells, as compared with the case where no such control was conducted.

Hereinabove, an explanation was made on the preferred embodiment and examples of the cell culture apparatus, the cell culture system and the cell culture apparatus of the present invention. However, the cell culture apparatus, the cell culture system and the cell culture method of the present invention are not limited to the above-mentioned embodiments, and it is needless to say various modifications are possible within the scope of the present invention.

For example, in the above-mentioned embodiment, a configuration is described in which the number of each of the culture medium storage container, the heating/gas controlling part, the container table, the monitoring apparatus or the like is one. However, the number of each of these devices is not limited to one, and they may be provided in a plural number.

INDUSTRIAL APPLICABILITY

The present invention is an invention relating to an apparatus for culturing cells. Therefore, the present invention can be used for an apparatus, a device or a system for culturing cells.

The invention claimed is:

1. A cell culture method comprising:

placing on an upper surface of a container table a culture container formed of a soft packing material;

dividing an enclosure part of the culture container into two or more chambers by placing on an upper surface of the culture container a movable partition roller so as to form a culture part for enclosing a culture medium and/or cells being cultured;

pressing the upper surface of the culture container with the partition roller such that a first inner surface of the culture container contacts a second inner surface of the culture container opposite the first inner surface so as to segregate the two or more chambers from each other; and changing a volume of the culture part by moving a rotation axis of the partition roller with the partition roller in a radial direction relative to the culture container, while allowing the partition roller to rotate and maintaining the partition roller to press the upper surface of the culture container such that the first inner surface of the culture container contacts the second inner surface of the culture container, wherein the two or more chambers comprise an extensible part, and the partition roller segregates the extensible part from the culture part so as to enclose an interior space of the culture part from the extensible part, and wherein a volume of an interior space of the culture part changes in a continuous manner while moving the partition roller and/or the culture container.

2. The cell culture method according to claim 1, further comprising:

moving the partition roller towards a tube for harvest that is attached to the culture container; and pushing the culture medium and/or the cells being culture enclosed in the enclosure part to the tube for harvest so as to send the culture medium and/or the cells being cultured to a harvest container connected to the tube for harvest.

3. The cell culture method according to claim a 1, wherein the two or more chambers are not intercommunicative by the culture medium and/or the cells from each other.

4. The cell culture method according to claim 1, wherein the culture container comprises an opening, and at least a tapered form in which a cross-section of an interior space of the culture container becomes gradually narrower towards the opening.

5. The cell culture method according to claim 1, further comprising:

measuring a condition of the culture medium and/or cells being cultured; and moving the partition roller and/or the culture container based on measurement results obtained by the measuring.

6. The cell culture method according to claim 1, wherein the dividing is performed by holding the culture container between the partition roller and a trough-like member, and wherein the trough-like member has an arc-shaped cross section and is provided outside an outer peripheral surface of the partition roller.

7. The cell culture method according to claim 6, further comprising:

pushing the enclosure part using an outer wall of the trough-like member when the partition roller moves.

8. The cell culture apparatus according to claim 7, wherein the trough-like member has a cylindrical shape, and an arc of the trough-like member and an outer peripheral circumference of the roller are concentrically formed.

9. The cell culture method according to claim 1, wherein an outer periphery of a cross section in a radial direction of the partition roller has a teeth-like structure, and each mountain part and each valley part of the teeth-like structure are in a straight line or in a curved line in an axial direction of the partition roller.

10. The cell culture method according to claim 1, wherein the dividing is performed by holding the culture container between two partition rollers.

11. The cell culture method according to claim 1, wherein the pressing is performed by applying a pressure of 0.1 MPa or more when the partition roller is placed on the upper surface of the culture container.

12. The cell culture method according to claim 1, wherein an outer peripheral surface of the partition roller is formed of at least one selected from the group consisting of urethane rubber, silicone rubber, and a thermoplastic resin.

13. The cell culture method according to claim 1, further comprising:
removing creases from the culture container placed on the upper surface of the container table using a holder.

14. The cell culture method according to claim 13, wherein the holder holds two sides of the culture container in an extensible part thereof to remove the creases.

15. The cell culture method according to claim 1, further comprising:
keeping the culture medium and or the cells being cultured enclosed within the culture container uniform.

16. The cell culture method according to claim 1, wherein a hardness of an outer peripheral surface of the partition roller is at least 90 or smaller when measured by a type A durometer in accordance with JIS K 6253.

* * * * *

UNITED STATES PATENT AND TRADEMARK OFFICE
CERTIFICATE OF CORRECTION

PATENT NO. : 9,441,193 B2  
APPLICATION NO. : 12/450481  
DATED : September 13, 2016  
INVENTOR(S) : Tanaka et al.

Page 1 of 1

It is certified that error appears in the above-identified patent and that said Letters Patent is hereby corrected as shown below:

In the Claims

Column 18, Claim 3, Line 42, delete "according to claim a 1" and insert -- according to claim 1 --.

Signed and Sealed this  
Seventh Day of February, 2017

Michelle K. Lee  
*Director of the United States Patent and Trademark Office*